United States Patent
Enomoto et al.

(10) Patent No.: US 10,154,825 B2
(45) Date of Patent: Dec. 18, 2018

(54) IMAGE PROCESSING DEVICE, RADIOGRAPHIC IMAGING SYSTEM, IMAGE PROCESSING METHOD, AND NON-TRANSITORY COMPUTER READABLE MEDIUM

(71) Applicant: FUJIFILM CORPORATION, Minato-ku, Tokyo (JP)

(72) Inventors: Jun Enomoto, Kanagawa (JP); Takashi Tajima, Kanagawa (JP); Yasufumi Oda, Kanagawa (JP); Takeshi Kuwabara, Kanagawa (JP); Daiki Harada, Kanagawa (JP); Yuichi Hosoi, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 383 days.

(21) Appl. No.: 15/050,470

(22) Filed: Feb. 23, 2016

(65) Prior Publication Data
US 2016/0249875 A1 Sep. 1, 2016

(30) Foreign Application Priority Data
Feb. 26, 2015 (JP) ................. 2015-037418

(51) Int. Cl.
*G01N 5/00* (2006.01)
*G01N 23/201* (2018.01)
(Continued)

(52) U.S. Cl.
CPC ............. *A61B 6/5282* (2013.01); *A61B 6/06* (2013.01); *A61B 6/4291* (2013.01); *A61B 6/465* (2013.01);
(Continued)

(58) Field of Classification Search
CPC ........... A47L 9/00; A61B 6/06; A61B 6/4291; A61B 6/465; A61B 6/467; A61B 6/5282;
(Continued)

(56) References Cited

U.S. PATENT DOCUMENTS 6,222,906 B1    4/2001   Sakaguchi et al.
8,649,587 B2 *   2/2014   Star-Lack ............. G06T 7/0012
                                                                                               378/7
(Continued)

FOREIGN PATENT DOCUMENTS

JP       S60-236594 A      11/1985
JP       H11-318877 A     11/1999
(Continued)

OTHER PUBLICATIONS

English language translation of the following: Office action dated Oct. 31, 2017 from the JPO in a Japanese patent application No. 2015-037418 corresponding to the instant patent application.

*Primary Examiner* — Irakli Kiknadze
(74) *Attorney, Agent, or Firm* — Solaris Intellectual Property Group, PLLC

(57) ABSTRACT

The present disclosure provides an image processing device including: a scattered radiation correction data acquisition section that acquires scattered radiation correction data as a result of radiation being irradiated onto a radiographic imaging device that images a radiographic image; a pixel region acquisition section that acquires information indicating a size of an effective pixel region of the radiographic imaging device; an exposure range acquisition section that acquires information indicating an imaging exposure range of radiation for imaging an imaging subject with the radiographic imaging device; an image data acquisition section that acquires image data as a result of imaging a radiographic image of the imaging subject; and a correction section that corrects the image data acquired by the image (Continued)

data acquisition section using the scattered radiation correction data, in a case in which the imaging exposure range includes an area outside of the effective pixel region.

19 Claims, 9 Drawing Sheets

(51) Int. Cl.
 *A61B 6/00* (2006.01)
 *A61B 6/06* (2006.01)
(52) U.S. Cl.
 CPC .............. *A61B 6/467* (2013.01); *A61B 6/542* (2013.01); *A61B 6/588* (2013.01); *A61B 6/548* (2013.01)
(58) Field of Classification Search
 CPC ......... A61B 6/542; A61B 6/548; A61B 6/588; A61B 6/03; A61B 5/14546; A61B 5/1455; A61B 2560/0223; A61B 5/0075; A61B 5/024; A61B 5/02416; A61B 5/02433; A61B 5/14532; A61B 5/1495; A61B 5/7203; A61B 5/7235; A61B 5/7253; A61B 5/7264; A61B 5/7267; A61B 5/149; G06T 11/005; A61K 2800/91; A61K 8/02; A61K 8/60; A61Q 19/08; A61Q 5/12; A61Q 7/00; G01S 17/003; G01S 17/58; G01S 17/95; G01S 7/497; G01S 17/87; G01S 17/89; G01S 7/481; G01S 7/491
 USPC .......................................... 378/4, 6, 7, 62, 70
 See application file for complete search history.

(56) References Cited

U.S. PATENT DOCUMENTS

| | | | | |
|---|---|---|---|---|
| 2008/0272309 | A1* | 11/2008 | Schweizer | ............ G01T 1/1648 250/394 |
| 2009/0190714 | A1* | 7/2009 | Partain | ................... A61B 6/032 378/19 |
| 2010/0080433 | A1* | 4/2010 | Noshi | .................. A61B 6/5282 382/131 |
| 2011/0158388 | A1* | 6/2011 | Hirooka | ................... A61B 6/00 378/62 |

FOREIGN PATENT DOCUMENTS

| | | |
|---|---|---|
| JP | 2005-321334 A | 11/2005 |
| JP | 2014-23691 A | 2/2014 |

\* cited by examiner

FIG.9
(1)
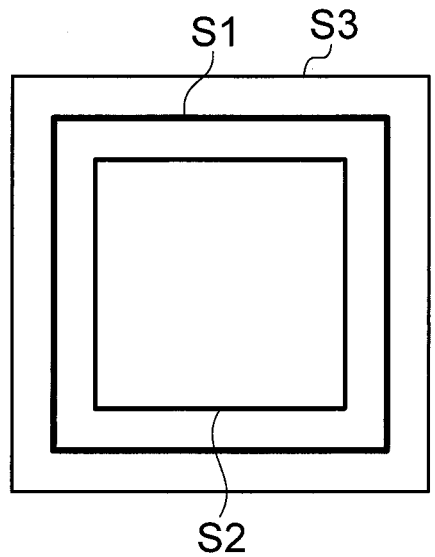
(2)
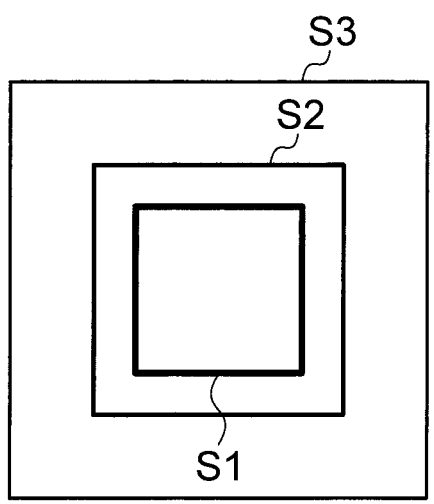

IMAGE PROCESSING DEVICE, RADIOGRAPHIC IMAGING SYSTEM, IMAGE PROCESSING METHOD, AND NON-TRANSITORY COMPUTER READABLE MEDIUM

CROSS-REFERENCE TO RELATED APPLICATION

This application claims priority under 35 USC 119 from Japanese Patent Application No. 2015-037418 filed on Feb. 26, 2015, the disclosure of which is incorporated by reference herein.

BACKGROUND

Technical Field

The present disclosure relates to an image processing device, a radiographic imaging system, an image processing method, and a non-transitory computer readable medium storing an image processing program.

Related Art

Conventionally, radiographic images are imaged by using the radiation detector that include a radiation detector containing pixels to detect radiation that has been irradiated from a radiation irradiation device and that has passed through an imaging subject.

Generally in radiographic imaging, scattered radiation occurs due to the radiation passing through the imaging subject, and thus the scattered radiation is included in the radiation that passes through the imaging subject. In a case in which scattered radiation is included in the radiation, a reduction in contrast and generation of artifacts in the radiographic image sometimes causes a deterioration in image quality.

Technology to eliminate the effects of scattered radiation on radiographic images is known (see, for example, Japanese Patent Application Laid-Open (JP-A) No. 2005-321334 and JP-A No. 2014-23691).

Scattered radiation occurs due to plural factors. In radiographic imaging, outside of an effective pixel region (a region of pixels contributing to radiographic imaging) of the radiographic imaging device (radiation detector), is also irradiated with radiation. In such cases, sometimes the radiation irradiated to the outside of the effective pixel region is, for example, reflected at the periphery of the radiographic imaging device (radiation detector), generating scattered radiation caused by external factors. Therefore, to improve the image quality of the radiographic images, it is desirable to prevent the effects of scattered radiation caused by external factors.

SUMMARY

The present invention provides an image processing device, a radiographic imaging system, an image processing method, and a non-transitory computer readable medium storing an image processing program that may prevent the effects of scattered radiation and that may improve image quality.

An image processing device according to a first aspect includes: a scattered radiation correction data acquisition section that acquires scattered radiation correction data as a result of radiation being irradiated onto a radiographic imaging device that images a radiographic image; a pixel region acquisition section that acquires information indicating a size of an effective pixel region of the radiographic imaging device; an exposure range acquisition section that acquires information indicating an imaging exposure range of radiation for imaging an imaging subject with the radiographic imaging device; an image data acquisition section that acquires image data as a result of imaging a radiographic image of the imaging subject; and a correction section that corrects the image data acquired by the image data acquisition section using the scattered radiation correction data acquired by the scattered radiation correction data acquisition section, in a case in which the imaging exposure range indicated by the information acquired by the exposure range acquisition section includes an area outside of the effective pixel region indicated by the information acquired by the pixel region acquisition section.

A second aspect is an image processing device including: a scattered radiation correction data acquisition section that acquires scattered radiation correction data as a result of radiation being irradiated onto a radiographic imaging device that images a radiographic image; a pixel region acquisition section that acquires information indicating a size of an effective pixel region of the radiographic imaging device; an exposure range acquisition section that acquires information indicating an imaging exposure range of radiation for imaging an imaging subject with the radiographic imaging device; an image data acquisition section that acquires image data as a result of imaging a radiographic image of the imaging subject; and a correction section that corrects the image data acquired by the image data acquisition section using the scattered radiation correction data acquired by the scattered radiation correction data acquisition section, in a case in which the imaging exposure range indicated by the information acquired by the exposure range acquisition section is larger than the effective pixel region indicated by the information acquired by the pixel region acquisition section.

According to a third aspect, in the image processing device of the above second aspect, the correction section may not correct the image data using the scattered radiation correction data, in a case in which the imaging exposure range is smaller than the effective pixel region.

According to a fourth aspect, in the image processing device of the above first and second aspects, the scattered radiation correction data acquisition section may further acquire information indicating a correction exposure range that was irradiated with radiation during acquisition of the scattered radiation correction data, and the correction section may correct the image data using the scattered radiation correction data based on the size of the correction exposure range and the size of the imaging exposure range.

According to a fifth aspect, in the image processing device of the above fourth aspect, the correction section may correct the image data using the scattered radiation correction data, in a case in which the correction exposure range is the same as the imaging exposure range.

According to a sixth aspect, in the image processing device of the above fourth and the fifth aspect, the correction section may correct the image data using the scattered radiation correction data that has been adjusted according to the size of the imaging exposure range, in a case in which the correction exposure range is larger than the imaging exposure range.

According to a seventh aspect, in the image processing device of the above the fourth to the sixth aspects, the correction section may perform specific processing, in a case in which the correction exposure range is smaller than the imaging exposure range.

According to an eighth aspect, in the image processing device of the above the fourth to the seventh aspects, there may be plural types of the scattered radiation correction data, corresponding to sizes of the correction exposure range, and correction section may correct the image data using the scattered radiation correction data of a type corresponding to the size of the correction exposure range.

According to a seventh aspect, in the image processing device of the above aspects, there may be plural types of the scattered radiation correction data, corresponding to imaging environment information indicating an imaging environment for imaging the radiographic image, and the correction section may correct the image data of the radiographic image using scattered radiation correction data of a type corresponding to the imaging environment information indicating an imaging environment in which the radiographic image was imaged.

A radiographic imaging system according to a tenth aspect includes: a radiation irradiation device including a radiation source and a collimator; a radiographic imaging device that images a radiographic image using radiation that was irradiated from the radiation irradiation device; and the image processing device of the above aspects, which performs image processing on image data of a radiographic image imaged using the radiographic imaging device.

An image processing method according to an eleventh aspect includes: acquiring, by a scattered radiation correction data acquisition section, scattered radiation correction data as a result of radiation being irradiated onto a radiographic imaging device that images a radiographic image; acquiring, by a pixel region acquisition section, information indicating a size of an effective pixel region of the radiographic imaging device; acquiring, by an exposure range acquisition section, information indicating an imaging exposure range of radiation for imaging an imaging subject using the radiographic imaging device; acquiring, by an image data acquisition section, image data as a result of imaging a radiographic image of the imaging subject; and correcting, by a correction section, the image data acquired by the image data acquisition section using the scattered radiation correction data acquired by the scattered radiation correction data acquisition section, in a case in which the imaging exposure range indicated by the information acquired by the exposure range acquisition section includes an area outside of the effective pixel region indicated by the information acquired by the pixel region acquisition section.

An image processing method according to the twelfth aspect includes: acquiring, by a scattered radiation correction data acquisition section, scattered radiation correction data as a result of radiation being irradiated onto a radiographic imaging device that images a radiographic image; acquiring, by a pixel region acquisition section, information indicating a size of an effective pixel region of the radiographic imaging device; acquiring, by an exposure range acquisition section, information indicating an imaging exposure range of radiation for imaging an imaging subject using the radiographic imaging device; acquiring, by an image data acquisition section, image data as a result of imaging a radiographic image of the imaging subject; and correcting, by a correction section, the image data acquired by the image data acquisition section using the scattered radiation correction data acquired by the scattered radiation correction data acquisition section, in a case in which the imaging exposure range indicated by the information acquired by the exposure range acquisition section is larger than the effective pixel region indicated by the information acquired by the pixel region acquisition section.

A thirteenth aspect is a non-transitory computer readable medium storing an image processing program that causes a computer to execute processing, the processing including: acquiring scattered radiation correction data as a result of radiation being irradiated onto a radiographic imaging device that images a radiographic image; acquiring information indicating a size of an effective pixel region of the radiographic imaging device; acquiring information indicating an imaging exposure range of radiation for imaging an imaging subject using the radiographic imaging device; acquiring image data as a result of imaging a radiographic image of the imaging subject; and correcting the image data using the scattered radiation correction data, in a case in which the imaging exposure range includes an area outside of the effective pixel region.

A fourteenth aspect is a non-transitory computer readable medium storing an image processing program that causes a computer to execute processing, the processing including acquiring scattered radiation correction data as a result of radiation being irradiated onto a radiographic imaging device that images a radiographic image; acquiring information indicating a size of an effective pixel region of the radiographic imaging device; acquiring information indicating an imaging exposure range of radiation for imaging an imaging subject using the radiographic imaging device; acquiring image data as a result of imaging a radiographic image of the imaging subject; and correcting the image data using the scattered radiation correction data, in a case in which the imaging exposure range is larger than the effective pixel region.

The above aspects may provide an image processing device, a radiographic imaging system, an image processing method, and a non-transitory computer readable medium storing an image processing program that may improve image quality of the radiographic image.

BRIEF DESCRIPTION OF THE DRAWINGS

Exemplary embodiments will be described in detail based on the following figures, wherein:

FIG. 9 is an explanatory diagram to explain a case in which an imaging exposure range>a correction exposure range.

DETAILED DESCRIPTION

Detailed explanation follows regarding an exemplary embodiment of the present disclosure, with reference to the drawings. Note that the present disclosure is not limited to the present exemplary embodiment.

Figure 1:
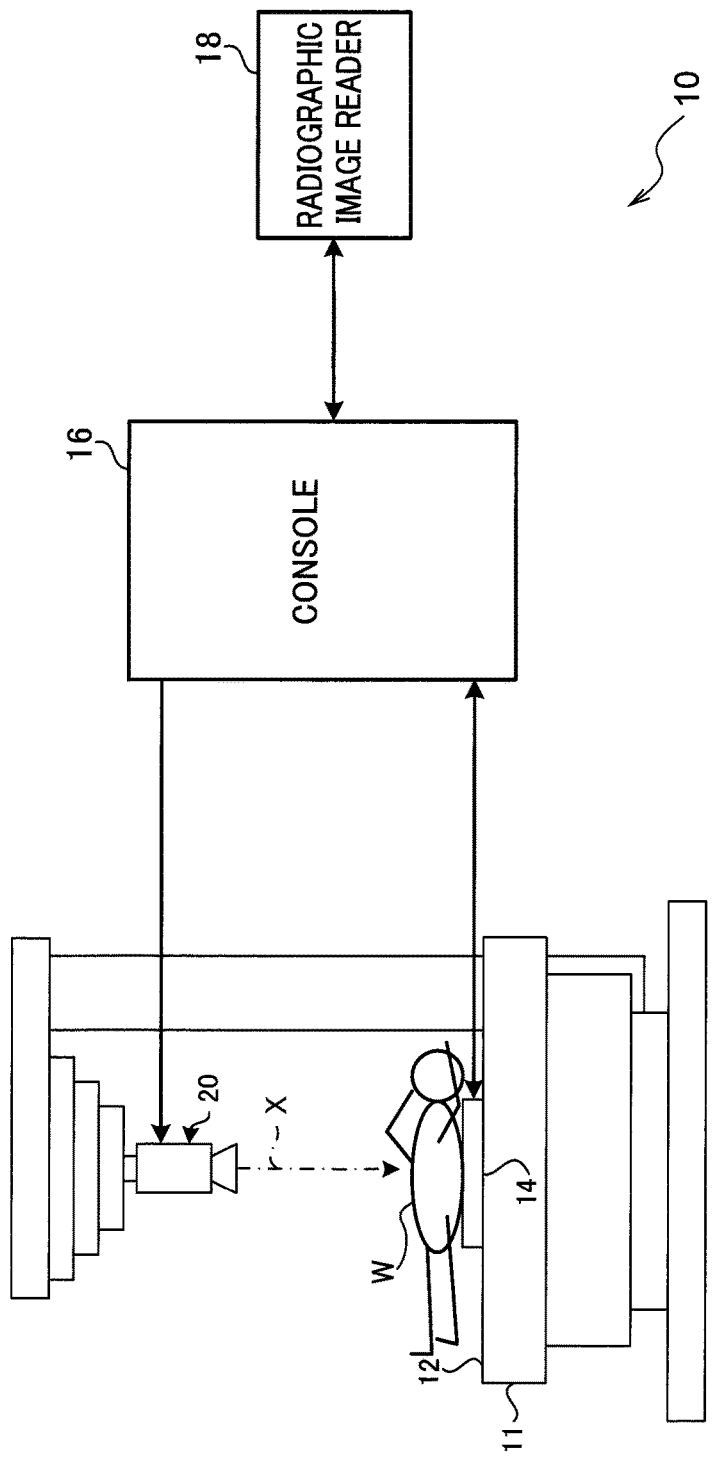
FIG. 1 is a schematic configuration diagram illustrating an outline of an overall configuration of a radiographic imaging system according to an exemplary embodiment.

First, explanation follows regarding schematic configuration of an overall radiographic imaging system of the present exemplary embodiment. FIG. 1 is a schematic configuration diagram of an overall configuration of a radiographic imaging system of the present exemplary embodiment.

A radiographic imaging system 10 of the present exemplary embodiment has a function of imaging radiographic images of a patient W, an example of an imaging subject, according to operation by a user such as a physician or a radiographer, based on instructions (an imaging menu) input from an external system (for example, a Radiology Information System: RIS) using a console 16.

The radiographic imaging system 10 of the present exemplary embodiment includes a radiographic imaging device 14, a console 16, a radiographic image reader 18, and a radiation irradiation device 20.

Explanation follows regarding a case in which in the radiographic imaging system 10 of the present exemplary embodiment, the console 16, this being an example of an image processing device for image data of radiographic images imaged by the radiographic imaging device 14, performs image processing, and in particular, performs correction processing to eliminate the effects of scattered radiation from the image data of a radiographic image. Note that in the present exemplary embodiment, the term "eliminate" is used since even in a case in which the effects of scattered radiation in the image data of the radiographic images are lessened, the effects are partially eliminated.

The radiation irradiation device 20 irradiates radiation X under control of the console 16. The radiation irradiation device 20 irradiates radiation X onto an imaging subject site of the patient W on an imaging face 12 of an imaging table 11 when imaging a radiographic image of the patient W. In a case in which irradiating radiation X from the radiation irradiation device 20, the center of an effective pixel region (described in detail later) of the radiographic imaging device 14 is preferably aligned with the center of an irradiation field. Accordingly, for example, configuration may be made in which the radiographic imaging device 14 includes a position sensor and a radiation irradiation section 62 ascertains the position of the radiographic imaging device 14, and prepares to irradiate the radiation X when the center positions overlap.

The radiographic imaging device 14 includes a radiation detector 28 (see FIG. 2 and FIG. 3), and generates charges according to the radiation amount of the radiation X, images a radiographic image based on the generated charges, and transmits image data of the radiographic image. In the present exemplary embodiment, an electronic cassette, for example a Digital Radiography (DR) cassette that converts radiation into digital data for output, is employed as a specific example of the radiographic imaging device 14.

In FIG. 1, the radiographic imaging device 14 is illustrated in a state disposed on the imaging face 12 of the imaging table 11.

The image data of the radiographic image imaged by the radiographic imaging device 14 is output to the console 16. The console 16 of the present exemplary embodiment controls the radiographic imaging device 14 and the radiation irradiation device 20 using, for example, an imaging menu and various information acquired from an external system or the like, through wireless communication or wired communication such as a Local Area Network (LAN). The console 16 of the present exemplary embodiment exchanges various information, including the image data of the radiographic image, with the radiographic imaging device 14. Further, the console 16 of the present exemplary embodiment performs image processing on the image data of the radiographic image acquired from the radiographic imaging device 14, and more specifically, performs correction processing to eliminate the effects of scattered radiation from the image data of the radiographic image. Further, the console 16 transmits the image data of the radiographic image acquired from the radiographic imaging device 14 and image data on which image processing has been performed to the radiographic image reader 18.

The radiographic image reader 18 displays image data of the radiographic images received from the console 16. A specific example of the radiographic image reader 18 is a viewer or the like. However there is no particular limitation thereto, and portable information terminal devices, known as personal digital assistants (PDAs), may be employed, with typical examples thereof being tablet terminals, smartphones, and the like.

Figure 2:
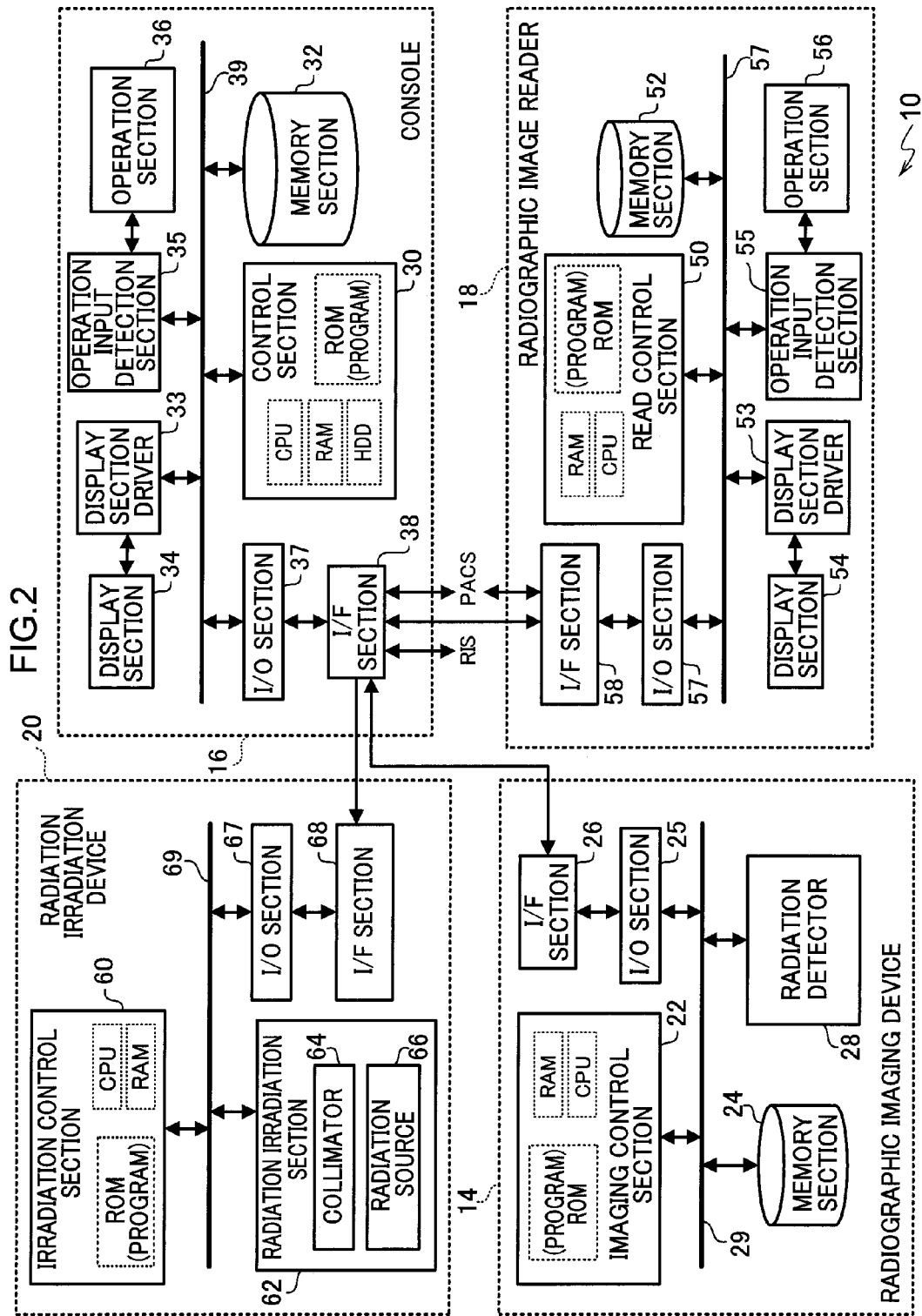
FIG. 2 is a functional block diagram illustrating a schematic configuration to explain functions of a radiographic imaging device, a console, a radiographic image reader, and a radiation irradiation device in a radiographic imaging system of the present exemplary embodiment.

FIG. 2 is a functional block diagram illustrating a schematic configuration in order to explain the functions of the radiographic imaging device 14, the console 16, the radiographic image reader 18, and the radiation irradiation device 20 of the radiographic imaging system 10 of the present exemplary embodiment.

The console 16 of the present exemplary embodiment is a server-computer. As illustrated in FIG. 2, the console 16 includes a control section 30, a memory section 32, a display section driver 33, a display section 34, an operation input detection section 35, an operation section 36, an input/output (I/O) section 37, and an interface (I/F) section 38. The control section 30, the memory section 32, the display section driver 33, the operation input detection section 35, and the I/O section 37 are connected to each other through a bus 39, for example a system bus or a control bus, so as to be capable of exchanging information and the like.

The control section 30 of the present exemplary embodiment is an example of a scattered radiation correction data acquisition section, a pixel region acquisition section, an exposure range acquisition section, an image data acquisition section, and a correction section. The control section 30 controls operation of the overall console 16. Further, the control section 30 performs image processing to eliminate the effects of scattered radiation in image data of the radiographic images. The control section 30 includes a central processing unit (CPU), read only memory (ROM), random access memory (RAM), and a hard disk drive (HDD). The CPU controls operation of the overall console 16. The ROM is stored in advance with various programs or the like, including an image processing program used by the CPU. The RAM temporarily stores various data. The HDD stores and retains various data. Note that the HDD may be a solid state drive (SDD), and may function as the memory section 32.

The display section driver 33 controls display of various information on the display section 34. The display section 34 of the present exemplary embodiment displays an imaging menu, radiographic images, and the like. The operation input detection section 35 detects operation states and process operations of the operation section 36. The operation section 36 is employed by the user to instruct radiographic imaging, image processing, and the like. The operation section 36 may, as an example, be in the format of a keyboard and a mouse, or may be in the format of a touch panel integrated together with the display section 34. The operation section 36 may also have a format including a camera, and be input with various instructions by the camera recognizing user gestures.

The I/O section 37 and the I/F section 38 exchanges various information with the radiographic imaging device 14, the radiographic image reader 18, the radiation irradiation device 20, an external system such as an RIS, and an external system such as a picture archiving and communication system (PACS), using wireless communication or wired communication.

The memory section 32 stores various data such as image data of radiographic images received from the radiographic imaging device 14, scattered radiation correction data, and the like.

The radiographic image reader 18 of the present exemplary embodiment includes a read control section 50, a memory section 52, a display section driver 53, a display section 54, an operation input detection section 55, an operation section 56, an I/O section 57, and an I/F section 58. The read control section 50, the memory section 52, the display section driver 53, the operation input detection section 55, and the I/O section 57 are connected to each other through a bus 59, for example a system bus or a control bus, so as to be capable of exchanging various information and the like.

The read control section 50 controls operation of the overall radiographic image reader 18. The read control section 50 includes a CPU, ROM, and RAM. The CPU controls operation of the overall radiographic image reader 18. The ROM is stored in advance with various processing programs and the like employed by the CPU. The RAM temporarily stores various data.

The display section driver 53, the display section 54, the operation input detection section 55, and the operation section 56 respectively have similar functions to the display section driver 33, the display section 34, the operation input detection section 35, and the operation section 36 of the console 16.

The I/O section 57 and the I/F section 58 communicates various information between the console 16 and the PACS using electromagnetic wireless communication, optical communication using light, wired communication, or the like.

The memory section 52 stores radiographic images received from the console 16. Non-volatile memory is a specific example of the memory section 52.

Figure 3:
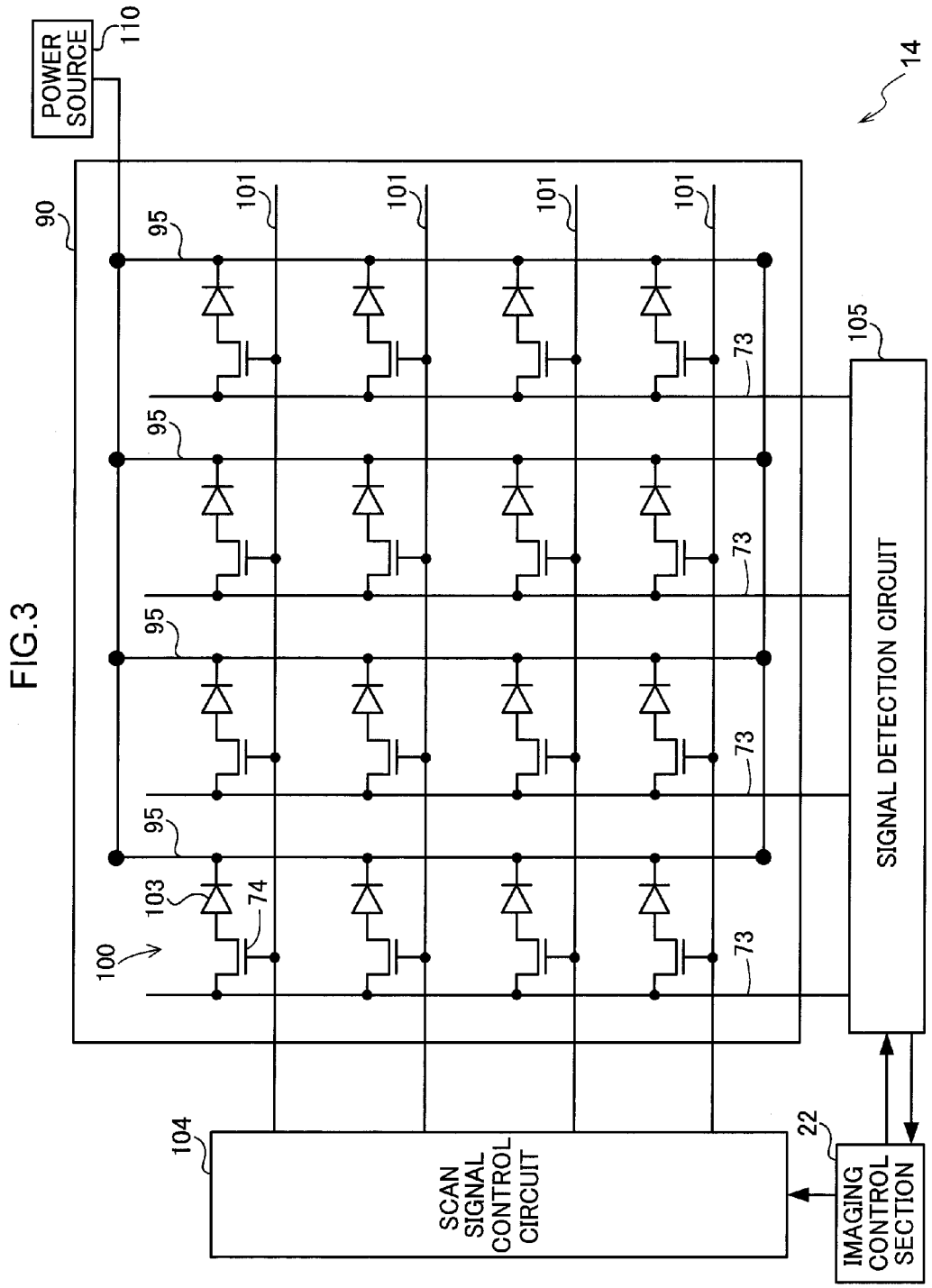
FIG. 3 is a configuration diagram illustrating configuration of a radiation detector of the present exemplary embodiment.

The radiographic imaging device 14 of the present exemplary embodiment includes an imaging control section 22, a memory section 24, an I/O section 25, an I/F section 26, the radiation detector 28, a shielding plate 97 (see FIG. 5), and a power source 110 (see FIG. 3). The imaging control section 22, the memory section 24, the I/O section 25, and the radiation detector 28 are connected to each other through a bus 29, for example a system bus or a control bus, so as to be capable of exchanging various information.

The imaging control section 22 controls operation of the overall radiographic imaging device 14, and includes a CPU, ROM, and RAM. The CPU controls operation of the overall radiographic imaging device 14. The ROM is stored in advance with various processing programs and the like that are used by the CPU. The RAM temporarily stores various data.

The memory section 24 stores various data such as image data of the radiographic images detected by the radiation detector 28.

The I/O section 25 and the I/F section 26 exchange various information, including image data of the radiographic images, with the console 16 using wireless communication or wired communication.

The radiation detector 28 is irradiated with the radiation X, records image data of a radiographic image, and outputs the recorded image data. As the image data, the radiation detector 28 detects the charges generated according to the radiation amount of the irradiated radiation X for each pixel.

FIG. 3 is a configuration diagram illustrating a configuration of the radiation detector 28 of the present exemplary embodiment. In the present exemplary embodiment, explanation is given regarding a case in which the present invention is applied with the indirect-conversion-type radiation detector 28 in which the radiation X is initially converted into light, and the converted light is then converted into charges. A scintillator 98 (see FIG. 5) that converts the radiation X into light is omitted from illustration in FIG. 3.

The radiation detector 28 of the present exemplary embodiment includes a thin film transistor (TFT) substrate 90 (see FIG. 5), the scintillator 98 (see FIG. 5), a scan signal control circuit 104, and a signal detection circuit 105.

The radiation detector 28 includes the TFT substrate 90 that includes pixels 100, each including: a sensor portion 103 that receives light, generates charges, and accumulates the generated charges; and a TFT switch 74 that is a switching element for reading the charges accumulated in the sensor portions 103. In the present exemplary embodiment, light converted by the scintillator 98 (see FIG. 5) is illuminated so as to generate charges in the sensor portions 103.

Plural pixels 100 are arrayed in a matrix formation along one direction (the direction of the gate lines in FIG. 3) and a direction intersecting with the gate line direction (the direction of the signal lines in FIG. 3). FIG. 3 illustrates a simplified array of the pixels 100; however, for example, 1024×1024 of the pixels are arrayed in the gate line direction and the signal line direction.

In the present exemplary embodiment, out of the pixels 100, a region formed by pixels 100 that actually contribute to radiographic imaging is referred to as the "effective pixel region". Note that the effective pixel region is a predetermined region, and disregards any pixels that do not contribute to radiographic imaging, such as pixels 100 within the effective pixel region that do not accumulate or read charges due to deterioration, manufacturing defects, or the like.

The TFT substrate 90 is formed as necessary with a protective film using an insulating material with low light absorbance, and the scintillator 98 (see FIG. 5), this being a radiation conversion layer, is affixed to the front face thereof using an adhesive resin with low light absorbance. The scintillator 98 is alternatively formed using a vacuum deposition method. The scintillator 98 preferably employs a scintillator that fluoresces over a comparatively broad wavelength region so as to enable generation of light in an absorbable wavelength region. Examples of materials for such a scintillator 98 include $CsI:Na$, $CaWO_4$, $YTaO_4:Nb$, $BaFX:Eu$ (wherein X is Br or Cl), or $LaOBr:Tm$ and GOS. Specifically, in a case in which imaging employs X-rays as the radiation X, a scintillator including cesium iodide (CsI) is preferable, and employing CsI:Tl (thallium-doped cesium iodide) or CsI:Na with a light emission spectrum of from 400 nm to 700 nm under the radiation X is particularly preferable. The emission peak wavelength of CsI:Tl in the visible light range is 565 nm. When a scintillator including CsI is employed for the scintillator 98, preferably an oblong shaped columnar crystal structure is formed using a vacuum deposition method.

The radiation detector 28 includes plural gate lines 101 for switching the TFT switches 74 ON and OFF, and plural signal lines 73 for reading the charges accumulated in the sensor portions 103. The gate lines 101 and the signal lines 73 intersects with each other.

The radiation detector 28 includes common electrode lines 95 alongside the respective signal lines 73. The sensor portions 103 are connected to the common electrode lines 95, and are applied with a bias voltage from the power source 110 in the radiographic imaging device 14 through the common electrode lines 95.

Control signals for switching the respective TFT switches 74 flow in the gate lines 101. The control signals flowing in the respective gate lines 101 switch the respective TFT switches 74.

Electrical signals corresponding to the charges accumulated in the respective pixels 100 flow in the signal lines 73 according to the switching state of the TFT switches 74 of the respective pixels 100.

A signal detection circuit 105 that detects the electrical signals flowing into the respective signal lines 73 is connected to the respective signal lines 73. The scan signal control circuit 104 that outputs control signals to the respective gate lines 101 to switch the TFT switches 74 ON and OFF is connected to the respective gate lines 101.

The signal detection circuit 105 and the scan signal control circuit 104 are connected to the imaging control section 22. The imaging control section 22 performs specific processing such as noise removal on digital signals converted in the signal detection circuit 105, outputs control signals indicating a timing for signal detection to the signal detection circuit 105, and outputs control signals indicating a timing for outputting scan signals to the scan signal control circuit 104.

The radiation irradiation device 20 of the present exemplary embodiment includes an irradiation control section 60, the radiation irradiation section 62, an I/O section 67, and an I/F section 68. The radiation irradiation section 62 includes a collimator 64 and a radiation source 66. The irradiation control section 60, the radiation irradiation section 62, and the I/O section 67 are connected to each other so as to be capable of exchanging information and the like through a bus 69 such as a system bus or a control bus.

The I/O section 67 and the I/F section 68 exchange various information relating to irradiation of the radiation X with the console 16 using wireless communication or wired communication.

The irradiation control section 60 controls operation of the overall radiation irradiation device 20, and includes a CPU, ROM, and RAM. The CPU controls operation of the overall radiation irradiation device 20. The ROM is stored in advance with various processing programs and the like that are employed by the CPU. The RAM temporarily stores various data.

The irradiation control section 60 controls the irradiation field of the irradiated radiation X by controlling the collimator 64 of the radiation irradiation section 62 under control from the console 16. Further, the irradiation control section 60 irradiates the radiation X from the radiation source 66 of the radiation irradiation section 62 under control from the console 16.

Figure 4:
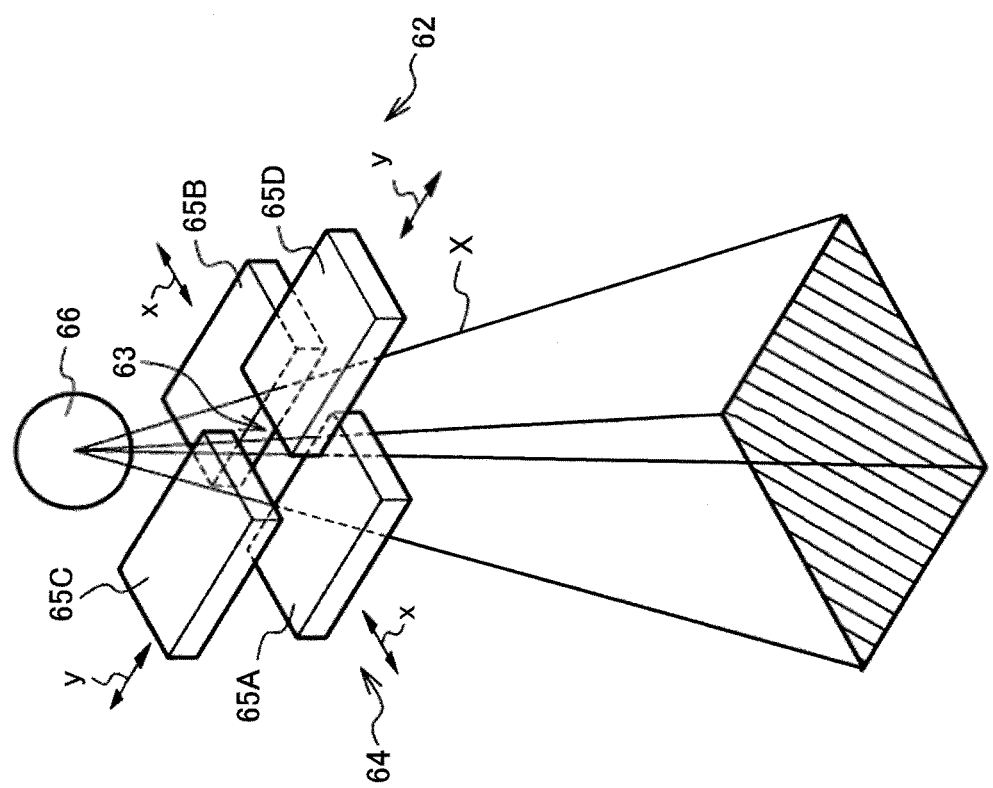
FIG. 4 is a perspective view illustrating configuration of relevant portions of a radiation irradiation section of the present exemplary embodiment.

FIG. 4 is a perspective view illustrating configuration of relevant portions of the radiation irradiation section 62 of the present exemplary embodiment. In the present exemplary embodiment, as a specific example, explanation is given regarding a case in which the collimator 64 is a four-bladed collimator.

As illustrated in FIG. 4, the collimator 64 is provided between the radiation source 66 and the radiographic imaging device 14, and includes four slit plates (blades) 65A, 65B, 65C, and 65D. Each of the slit plates 65A to 65D employs a radiation X blocking material such as lead or tungsten, and is configured by a plate shaped member that is rectangular in plan view. In the collimator 64, one side face of each of the slit plate 65A and the slit plate 65B face each other, and one side face of each of the slit plate 65C and the slit plate 65D face each other. In the collimator 64, the respective side faces that face each other in the respective slit plates 65A to 65D form an opening 63 with a rectangular shape in plan view.

In the radiation irradiation section 62, each of the slit plates 65A to 65D moves in response to a drive section including a motor or the like, omitted from illustration in the drawings. The slit plate 65A and the slit plate 65B can move along the x direction in FIG. 4, and the slit plate 65C and the slit plate 65D can move along the y direction in FIG. 4, this being a direction intersecting with the x direction mentioned above. Note that in the collimator 64, the movable range of the respective slit plates 65A to 65D is a range between a state in which leading end portions of the respective slit plates disposed facing each other are in contact with each other, namely a fully closed state of the opening 63, and a state of the maximum area at which the opening 63 maintains a rectangular shape in plan view. The size of the irradiation field is a size (area) corresponding to the size (area) of the opening 63. Note that in the present exemplary embodiment, the size of the irradiation field refers to the size of the area of a position equivalent to a detection face (a face irradiated with the radiation X) of the radiation detector 28 of the radiographic imaging device 14.

Next, explanation follows regarding image processing by the console 16 of the radiographic imaging system 10 of the present exemplary embodiment to eliminate the effects of scattered radiation on the image data of the radiographic image, with reference to the figures.

Figure 5:
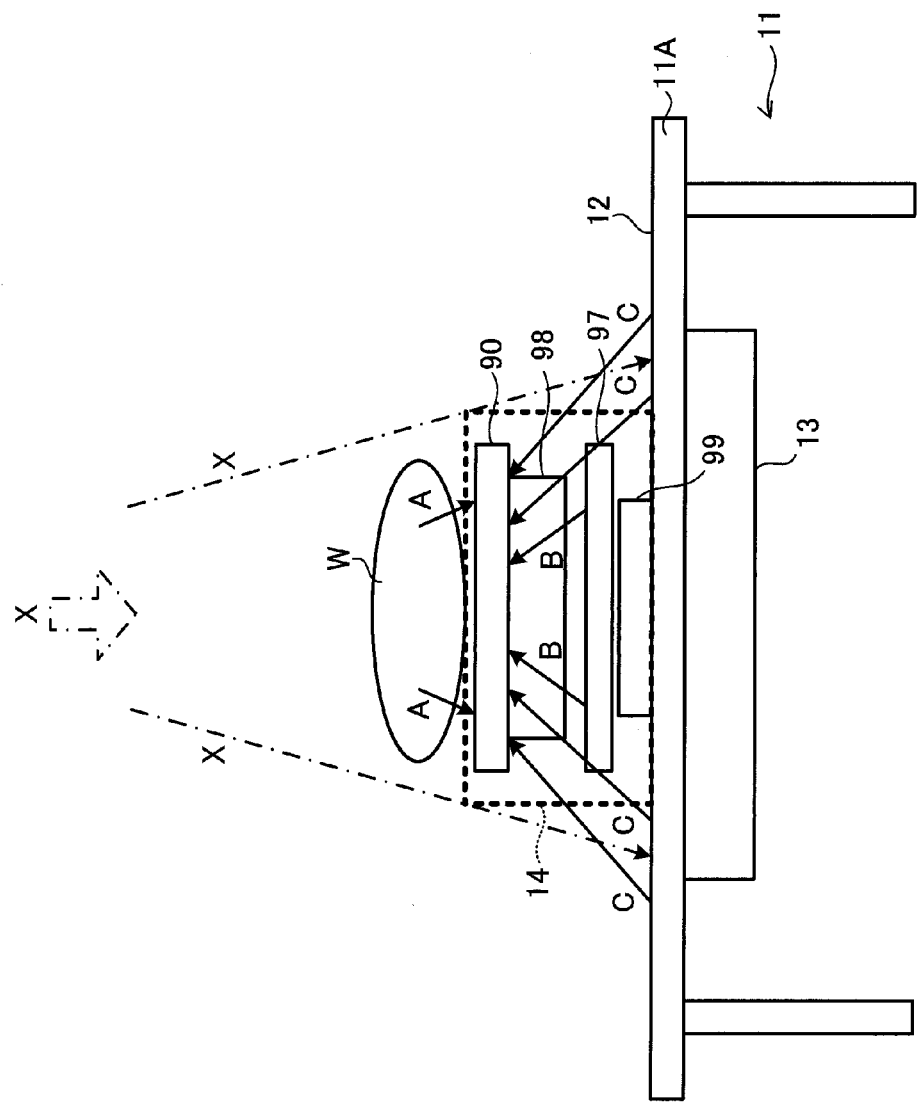
FIG. 5 is an explanatory diagram to explain scattered radiation generated during radiographic imaging.

First, explanation follows regarding the scattered radiation generated during radiographic imaging. FIG. 5 is an explanatory diagram to explain the scattered radiation generated during radiographic imaging. FIG. 5 illustrates a case in which the radiographic imaging device 14 is disposed on the imaging face 12 of a top plate 11A of the imaging table 11, between the imaging face 12 and the patient W.

The radiographic imaging device 14 includes the TFT substrate 90 and the scintillator 98 of the radiation detector 28 described above, the shielding plate 97, and an electrical section 99 inside a casing (not illustrated in the drawings). The electrical section 99 includes circuits such as the signal detection circuit 105 and the scan signal control circuit 104 included in the imaging control section 22 and the radiation detector 28. The shielding plate 97 is provided in order to shield the electrical section 99 from being irradiated with radiation X that has passed through the TFT substrate 90 and the scintillator 98, and is, for example, a metal sheet. The casing employs a frame made from carbon and a metal such as Mg.

The imaging table 11 includes the top plate 11A and a housing section 13. The material of the top plate 11A is, for example, acrylic. The housing section 13 houses the radiographic imaging device 14. Note that as described above, the state in FIG. 5 illustrates a case in which the radiographic imaging device 14 is not housed in the housing section 13, but is placed on the top plate 11A to perform radiographic imaging. The material of the housing section 13 is, for example, a metal.

In a case in which the radiation X is irradiated from the radiation irradiation device 20 toward the patient W, the scattered radiation that is incident to the radiographic imaging device 14 includes three types of scattered radiation A, B, and C, as illustrated in FIG. 5.

The scattered radiation A is scattered radiation generated by the patient W. The scattered radiation B is scattered radiation caused by the radiographic imaging device 14. The scattered radiation C is scattered radiation caused by external factors such as the imaging environment, including devices present around the imaging table 11. In the present exemplary embodiment, the scattered radiation C is referred to as "external scattered radiation" so as to distinguish it from other types of scattered radiation.

Regarding the scattered radiation A, generally imaging is performed employing a physical grid to eliminate the scattered radiation, or image processing is performed on the image data of the radiographic image using a virtual grid to eliminate the effects of the scattered radiation A.

Regarding the scattered radiation B, generally scattering is reduced by configuring the materials of the radiographic imaging device 14, and in particular the shielding plate 97, from materials that prevents the generation of scattered radiation. Note that generally, in metals, the higher the atomic number, the more readily scattered radiation is generated.

Note that when considering cases in which a small radiographic imaging device 14 (an electronic cassette) is employed, cases in which the ends of the radiographic imaging device 14 are hidden by the imaging subject (patient W), and so on, there is a tendency for the person, such as a technician carrying out imaging, to widen the irradiation field to greater than the effective pixel region and irradiate the radiation X, in order to reduce the risk of having to repeat imaging due to defects in edge portions of the radiographic image resulting from an excessively narrow irradiation field. Moreover, there is also a tendency for the person carrying out imaging to widen the irradiation field to greater than the effective pixel region and irradiate the radiation X since narrowing down the irradiation field to very close to the effective pixel region requires accurate alignment of the positions of the radiation source 66 and the radiographic imaging device 14 (the radiation detector 28). External scattered radiation (scattered radiation C) is liable to be generated in a case in which the irradiation field is widened to greater than the effective pixel region in this manner. For example, there is an increased risk of external scattered radiation from the imaging table 11, the housing section 13, and the floor and walls behind the imaging table 11 and the like, that are positioned around the radiographic imaging device 14, entering the radiographic imaging device 14 (radiation detector 28) from behind. Since the casing of the radiographic imaging device 14 is generally made from metal, there is also an increased risk of external scattered radiation from the casing entering the radiographic imaging device 14 (radiation detector 28) from behind. The external scattered radiation therefore results in effects such as a reduction in contrast and artifacts in radiographic images.

External scattered radiation can differ according to external factors due to the imaging environment, such as the imaging position (for example standing, recumbent, or free (including at the bedside)), the imaging room, and the like. It is accordingly desirable to eliminate the effects of external scattered radiation, including taking such factors into account.

As described above, recently, imaging employing virtual grids is attracting attention. In imaging employing virtual grids, scattered radiation A inside the patient W, this being the imaging subject, is estimated and eliminated from the radiographic image. However, in a state in which scattered radiation components due to the scattered radiation B and external scattered radiation are superimposed, these are determined to be scattered radiation A and eliminated. In order to accurately ascertain the scattered radiation component caused by the scattered radiation A, it is necessary to isolate the scattered radiation components caused by the scattered radiation B and external scattered radiation, and in particular, to isolate the scattered radiation component caused by external scattered radiation. Accurately ascertaining the scattered radiation component caused by the scattered radiation A and utilizing this in subsequent imaging enables what is referred to as smart imaging that reduces imaging time even under different imaging environments (external factors) such as imaging rooms.

Accordingly, in the console 16 of the radiographic imaging system 10 of the present exemplary embodiment, image processing is performed to eliminate the effects of scattered radiation from image data of the radiographic images.

Figure 6:
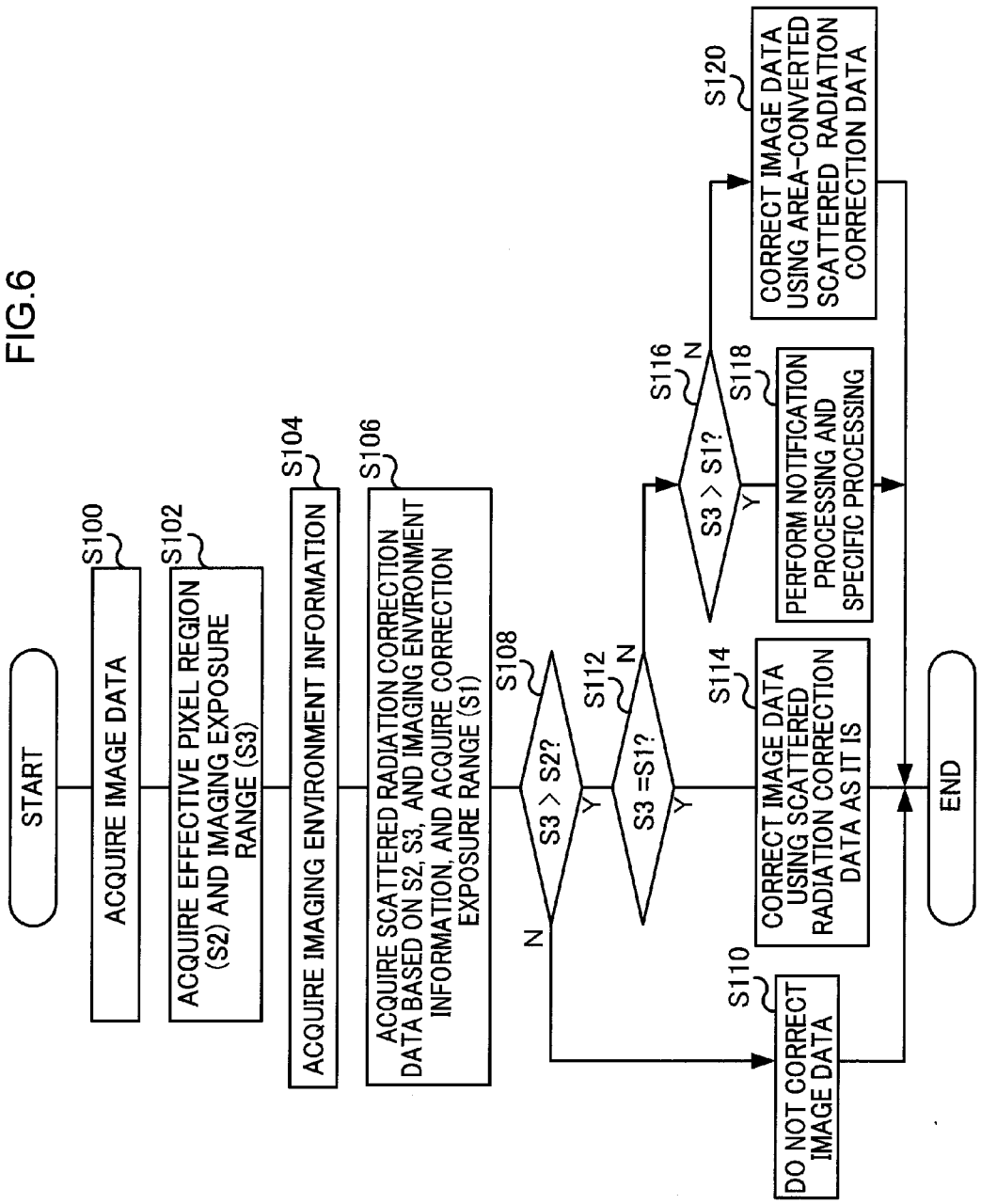
FIG. 6 is a flowchart illustrating image processing performed by a console of the present exemplary embodiment.

FIG. 6 is a flowchart illustrating an example of image processing executed by the console 16 of the present exemplary embodiment. In the radiographic imaging system 10 of the present exemplary embodiment, prior to the image processing illustrated in FIG. 6, the console 16 pre-acquires scattered radiation correction data for removing the effects of external scattered radiation from the radiographic images. The method for acquiring the scattered radiation correction data is not particularly limited, and for example, the scattered radiation correction data may be generated based on image data of a radiographic image obtained by irradiating the radiographic imaging device 14 with radiation X from the radiation irradiation device 20 in a state in which the patient W is not present.

The amount of external scattered radiation generated differs depending on the size of a correction exposure range, this being the irradiation field during acquisition of the scattered radiation correction data, and more specifically, depending on the size of the correction exposure range outside the effective pixel region of the radiographic imaging device 14. Accordingly, in the present exemplary embodiment, scattered radiation correction data includes plural types of scattered radiation correction data for each correction exposure range size, and are stored in the memory section 32 associated with the size of the correction exposure range. In the following explanation, the size of the correction exposure range is referred to as the "correction exposure range S1", and the size of the effective pixel region is referred to as the "effective pixel region S2".

In the present exemplary embodiment, in consideration of external factors, the scattered radiation correction data also includes plural types of scattered radiation correction data for each imaging environment (imaging room, imaging table 11, and imaging state (recumbent, standing, free)), and the scattered radiation correction data is stored associated with imaging environment information indicating the imaging environment. Moreover, in the present exemplary embodiment, the amount of scattered radiation generated differs depending on the tube voltage of the radiation source 66, and the scattered radiation correction data includes plural types of scattered radiation correction data for each tube voltage of the radiation source 66, and the scattered radiation correction data is stored associated with the tube voltage.

Namely, in the console 16 of the present exemplary embodiment, the memory section 32 is stored in advance with plural types of scattered radiation correction data associated with correction exposure ranges S1, imaging environment information, and tube voltages.

Note that such scattered radiation correction data may be stored in an external system instead of being stored in the memory section 32 within the console 16. The scattered radiation correction data may also be acquired from a separate console to the console 16 that images the patient W.

Note that the method for acquiring the scattered radiation correction data is not limited to the above, and for example, the scattered radiation correction data may be acquired in a state in which a phantom or the like corresponding to the patient W is present. A phantom or the like is preferably present since it enables external scattered radiation scattered by the patient W and reflected by the imaging table 11 (top plate 11A) and the like to be taken into account.

The image processing illustrated in FIG. 6 is executed by the control section 30 of the console 16 in a state in which the scattered radiation correction data is stored in the memory section 32 in this manner.

At step S100, the control section 30 uses the I/O section 37 and the I/F section 38 to acquire image data of a radiographic image from the radiographic imaging device 14. When, under control of the console 16, the patient W is irradiated with the radiation X from the radiation irradiation device 20, a radiographic image is imaged by the radiographic imaging device 14, and the console 16 acquires image data of the imaged radiographic image. Note that there is no particular limitation to where the control section 30 acquires the image data of the radiographic image from, and for example, the control section 30 may acquire the image data of the radiographic image from an external system such as a PACS instead of from the radiographic imaging device 14.

At the next step S102, the control section 30 acquires information indicating the effective pixel region S2 and the size of an imaging exposure range (referred to below as the imaging exposure range S3) of the radiation detector 28 of the radiographic imaging device 14. In the present exemplary embodiment, the imaging exposure range S3 is the size of the irradiation field during radiographic imaging of the patient W. The effective pixel region S2 is defined for each radiographic imaging device 14. The control section 30 may acquire the information indicating the effective pixel region S2 of the radiographic imaging device 14 used in imaging from an external system such as an RIS using the I/O section 37 and the I/F section 38, or may acquire the information indicating the effective pixel region S2 from the radiographic imaging device 14. Further, the control section 30 may acquire the information indicating the imaging exposure range S3 from an imaging menu when it is included in the imaging menu, or may acquire the information indicating the imaging exposure range S3 from an external system such as an RIS or from the radiation irradiation device 20 using the I/O section 37 and the I/F section 38. Further, the control section 30 may compute the imaging exposure range S3 according to a source image distance (SID) obtained based on the position of the radiation source 66 and the position of the radiographic imaging device 14, and an aperture ratio of the opening 63 of the collimator 64.

At the next step S104, the control section 30 acquires the imaging environment information. As described above, the imaging environment information is information indicating the imaging environment, this being an external factor that generates external scattered radiation. The control section 30 may acquire the imaging environment information from the imaging menu in a case in which it is included in the imaging menu, or may acquire the imaging environment information from an external system such as an RIS using the I/O section 37 and the I/F section 38.

At the next step S106, the control section 30 acquires the scattered radiation correction data and the correction exposure range S1 from the memory section 32 based on the effective pixel region S2, the imaging exposure range S3, and the imaging environment information. Note that at step S106, in a case in which there are plural combinations of scattered radiation correction data and correction exposure range S1 corresponding to the effective pixel region S2, the imaging exposure range S3, and the imaging environment information, plural pairs of scattered radiation correction data and correction exposure ranges S1 are acquired.

At the next step S108, the control section 30 determines whether or not the imaging exposure range S3 is larger than the effective pixel region S2 (imaging exposure range S3>effective pixel region S2). Processing proceeds to step S110 in a case in which the imaging exposure range S3 is not larger than the effective pixel region S2, namely, in a case in which the imaging exposure range S3 is smaller than the effective pixel region S2, and in a case in which the imaging exposure range S3 and the effective pixel region S2 are equal to each other. In the present exemplary embodiment, the correction exposure range S1, the effective pixel region S2, and the imaging exposure range S3 being "equal" refers to being equal to within a margin of error. "Larger" refers to being larger than in cases that are "equal", and "smaller" refers to being smaller than in cases that are "equal".

Figure 7:
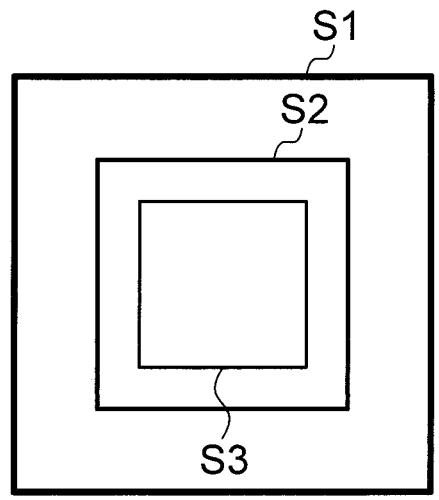
FIG. 7 is an explanatory diagram to explain a case in which an imaging exposure range<an effective pixel region<a correction exposure range.

At step S110, the control section 30 ends the current processing without correcting the image data of the radiographic image. Cases in which the imaging exposure range S3 is smaller than the effective pixel region S2 include, for example, cases in which imaging exposure range S3<effective pixel region S2<correction exposure range S1, as illustrated in FIG. 7. Moreover, cases in which effective pixel region S2>correction exposure range S1>imaging exposure range S3, and cases in which effective pixel region S2>imaging exposure range S3>correction exposure range S1 are also included. It is sufficient that imaging exposure range S3>correction exposure range S1, irrespective of the size of the correction exposure range S1.

In a case in which the imaging exposure range S3 is smaller than the effective pixel region S2, since the radiation X is not irradiated outside of the effective pixel region, there are no effects from external scattered radiation, or any such effects are considered minor, so in the present exemplary embodiment the image data is not corrected using the scattered radiation correction data.

At step S108, processing proceeds to step S112 in a case in which the imaging exposure range S3 is larger than the effective pixel region S2.

Figure 8:
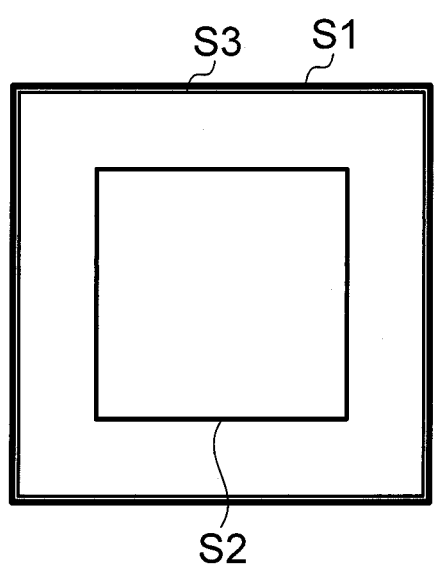
FIG. 8 is an explanatory diagram to explain a case in which an imaging exposure range=a correction exposure range.

At step S112, the control section 30 determines whether or not the imaging exposure range S3 is equal to the correction exposure range S1 (imaging exposure range S3=correction exposure range S1, see FIG. 8). Note that in a case in which plural correction exposure ranges S1 have been acquired, determination is made as to whether or not the correction exposure ranges S1 include a correction exposure range S1 that is equal to the imaging exposure range S3. Processing proceeds to step S114 in a case in which the imaging exposure range S3 is equal to the correction exposure range S1.

At step S114, the control section 30 corrects the image data of the radiographic image employing the scattered radiation correction data corresponding to the correction exposure range S1 for which imaging exposure range S3=correction exposure range S1 as it is, and then ends the current processing. Note that, in the present exemplary embodiment, the corrected image data is stored in the memory section 32.

At step S112, processing proceeds to step S116 in a case in which the imaging exposure range S3 is not equal to the correction exposure range S1. At step S116, the control section 30 determines whether or not the imaging exposure range S3 is larger than the correction exposure range S1 (imaging exposure range S3>correction exposure range S1). In a case in which plural correction exposure ranges S1 have been acquired, determination is made as to whether or not the imaging exposure range S3 is larger than the largest correction exposure range S1 out of the plural correction exposure ranges S1 that have been acquired. Processing proceeds to step S118 in a case in which the imaging exposure range S3 is larger than the correction exposure range S1.

As illustrated in (1) of FIG. 9, for example, cases in which the imaging exposure range S3 is larger than the correction exposure range S1 include cases in which imaging exposure range S3>correction exposure range S1>effective pixel region S2. Moreover, as illustrated in (2) of FIG. 9, for example, cases in which imaging exposure range S3>effective pixel region S2>correction exposure range S1 are also included. In a case in which the imaging exposure range S3 is larger than the correction exposure range S1, there are concerns that appropriate correction may not be possible even when the image data of the radiographic image is corrected using the scattered radiation correction data corresponding to the correction exposure range S1.

Accordingly, at step S118, the control section 30 uses the display section 34 to notify the user with information indicating that the imaging exposure range S3 is larger than the correction exposure range S1, and ends the current processing after performing specific processing. The specific processing is not particularly limited. For example, in a case in which the imaging exposure range S3 is larger than the correction exposure range S1, the scattered radiation correction data is preferably acquired afresh in a state with a correction exposure range S1 set appropriately for the imaging exposure range S3. Accordingly, the control section 30 may display information on the display section 34 to prompt fresh acquisition of the scattered radiation correction data. Moreover, for example, in a case in which the imaging exposure range S3 is larger than the correction exposure range S1, the imaging exposure range S3 may be adjusted to the correction exposure range S1 and imaging (re-imaging) of the patient W performed. Accordingly, the control section 30 may display information on the display section 34 to prompt re-imaging. Moreover, for example, the present processing may be ended with no further action. Moreover, for example, the control section 30 may correct the image data of the radiographic image using the correction exposure range S1 with the size closest to that of the imaging exposure range S3. Note that in a case in which correction is performed in this manner, there are concerns of appropriate correction not being performed, and so the control section 30 preferably displays information to this effect, or information prompting user confirmation, on the display section 34.

At step S116, processing proceeds to step S120 in a case in which the imaging exposure range S3 is smaller than the correction exposure range S1.

Figure 10:
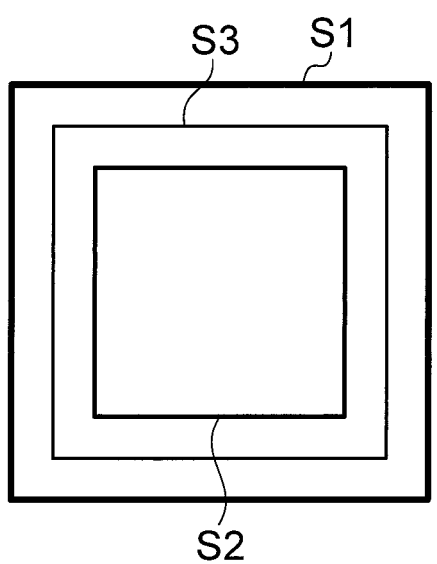
FIG. 10 is an explanatory diagram to explain a case in which a correction exposure range>an imaging exposure range>an effective pixel region.

Cases in which the imaging exposure range S3 is smaller than the correction exposure range S1 include, for example, cases in which correction exposure range S1>imaging exposure range S3>effective pixel region S2, as illustrated in FIG. 10.

At step S120, since the correction exposure range S1 is larger than the imaging exposure range S3, the control section 30 adjusts the scattered radiation correction data corresponding to the correction exposure range S1 to the size of the imaging exposure range S3, and specifically, performs area conversion with the scattered radiation correction data adjusted for the size of the imaging exposure range S3. The control section 30 employs the area-converted scattered radiation correction data to correct the image data of the radiographic image, before ending the current processing. Note that, in a case in which plural correction exposure ranges S1 have been acquired, the area conversion is preferably performed using the scattered radiation correction data corresponding to the plural correction exposure ranges S1. The area conversion method is not particularly limited, and, for example, may be generation by performing interpolation that employs both items of scattered radiation correction data in a case in which scattered radiation correction data corresponding to a correction exposure range S1 that is larger than the imaging exposure range S3, and scattered radiation correction data corresponding to a correction exposure range S1 that is smaller than the imaging exposure range S3 are both present.

In the console 16 of the present exemplary embodiment, the image data of the radiographic image subjected to the image processing illustrated in FIG. 6 is then subjected to other image processing. The other image processing includes, for example, radiographic image data correction employing a virtual grid to eliminate the effects of the scattered radiation A, as described above.

The image data of the radiographic image that has been corrected in this manner is stored in the memory section 32 of the console 16, or in an external system such as a PACS. The image data of the radiographic image is transmitted to the radiographic image reader 18 and displayed on the display section 54 of the radiographic image reader 18 as desired by the user.

As described above, in the console 16 of the radiographic imaging system 10 of the present exemplary embodiment, the scattered radiation correction data for eliminating the effects of external scattered radiation is acquired in advance, and the acquired scattered radiation correction data is associated with the correction exposure range S1 and stored in the memory section 32. The console 16 performs image processing to eliminate the effects of external scattered radiation on the image data of the radiographic image imaged by the radiographic imaging device 14 by irradiating the patient W with the radiation X from the radiation irradiation device 20. In a case in which the imaging exposure range S3 is not larger than the effective pixel region S2, the control section 30 of the console 16 does not correct the image data of the radiographic images using the scattered radiation correction data. In a case in which the imaging exposure range S3 is larger than the effective pixel region S2, and the imaging exposure range S3 is equal to the correction exposure range S1, the control section 30 corrects the image data of the radiographic images using the scattered radiation correction data as it is. In a case in which the imaging exposure range S3 is larger than the effective pixel region S2, and is larger than the correction exposure range S1, the control section 30 performs notification processing to express this fact, and performs specific processing. In a case in which the imaging exposure range S3 is larger than the effective pixel region S2, and smaller than the correction exposure range S1, the control section 30 converts the area of the scattered radiation correction data corresponding to the correction exposure range S1 according to the imaging exposure range S3, and corrects the image data of the radiographic image using the area-converted scattered radiation correction data.

Accordingly, in the console 16 of the radiographic imaging system 10 of the present exemplary embodiment, determination is made as to whether or not to perform correction (correction to eliminate the effects of external scattered radiation) on the image data of the radiographic image according to the imaging exposure range S3 and the effective pixel region S2. Moreover, in a case in which the imaging exposure range S3 is not larger than the effective pixel region S2, since there are no effects from external scattered radiation, or any such effects are considered minor, the image data of the radiographic image is not corrected. Accordingly, the present exemplary embodiment may reduce the time required for image processing.

In a case in which the imaging exposure range S3 is larger than the effective pixel region S2, the console 16 corrects the image data of the radiographic image using the scattered radiation correction data according to the size of the imaging exposure range S3 and the correction exposure range S1.

Accordingly, the present exemplary embodiment may eliminate the effects of the external scattered radiation from the image data of the radiographic image, appropriately. Accordingly, the present exemplary embodiment may suppress the generation of artifacts and the like in the radiographic image, and may improve the image quality of the radiographic image.

In the exemplary embodiment, since the effects of external scattered radiation may be eliminated from the image data of the radiographic image appropriately, in a case in which image processing is performed to eliminate the effects of the scattered radiation A using a virtual grid, the scattered radiation A can be estimated appropriately by performing the image processing using a virtual grid after the effects of external scattered radiation have been eliminated. Accordingly, the present exemplary embodiment may eliminate the effects of the scattered radiation A.

In the present exemplary embodiment, plural types of scattered radiation correction data exist for each imaging environment, taking into consideration external factors (at least one of the imaging room, the imaging table 11, and the imaging state (recumbent, standing, free and the like)). The control section 30 of the console 16 corrects the image data of the radiographic image using the scattered radiation correction data according to the acquired imaging environment information. Accordingly, the present exemplary embodiment may more appropriately eliminate the effects of external scattered radiation.

In the above exemplary embodiment, a case in which correction is performed when the imaging exposure range S3 is larger than the effective pixel region S2, has been described. However, there is no limitation thereto. For example, even in a case in which the imaging exposure range S3 and the effective pixel region S2 are equal to each other, sometimes an area outside of the effective pixel region S2 is included in the imaging exposure range S3 in a case in which the shape of the imaging exposure range S3 and the shape of the effective pixel region S2 are different to each other, or cases in which their central positions are offset. In such cases, there is a concern of external scattered radiation occurring at portions outside the effective pixel region S2, and so image data of the radiographic image is preferably corrected using the scattered radiation correction data. In such cases, determination as to whether or not to correct the image data of the radiographic image using the scattered radiation correction data may be made based on whether or not an area outside of the effective pixel region S2 is included in the imaging exposure range S3.

In the above exemplary embodiment, a case in which the processing of step S108 is performed with priority over steps S112 and S116 of the image processing, has been described. However, the processing priority sequence is not limited thereto. For example, the processing of step S112 may be given priority over the processing of step S108. In such a configuration, the image data is corrected by the processing of step S114 in a case in which the imaging exposure range S3 and the effective pixel region S2 have been determined to be equal to each other by the processing of step S112. Moreover, in a case in which the imaging exposure range S3 and the effective pixel region S2 are not equal to each other, the image data need not be corrected by the processing of step S110 in a case in which it has been determined by the processing of S108 that the imaging exposure range S3 is not larger than the effective pixel region S2.

In the above exemplary embodiment, a case in which the irradiation field is rectangular shaped, has been described. However, there is no limitation thereto. The irradiation field may be circular in shape. Moreover, for example, a multileaf collimator may be employed as the collimator 64.

In the exemplary embodiment described above, a case in which the radiographic imaging device 14 is disposed on the imaging face 12 of the imaging table 11, between the imaging face 12 and the patient W, and radiographic imaging is performed, has been described. However, the placement of the radiographic imaging device 14 is not limited thereto. For example, the radiographic imaging device 14 may perform imaging in a state housed inside the housing section 13. In the exemplary embodiment described above, a case in which the patient W is recumbent, has been described. However there is no limitation thereto, and the patient W may be sitting. Moreover, it goes without saying that, for example, application may be made to radiographic imaging using a medical trolley.

The radiographic imaging device 14 is not limited to that of the present exemplary embodiment. For example, in the present exemplary embodiment, as illustrated in FIG. 5, a case in which the radiographic imaging device 14 is what is referred to as an Irradiation Side Sampling (ISS) type that is irradiated with the radiation X from the TFT substrate 90 side, has been described. However, the radiographic imaging device 14 may be what is referred to as a Penetration Side Sampling (PSS) type that is irradiated with the radiation X from the scintillator 98 side. In the above present exemplary embodiment, explanation has been given regarding a configuration provided with the indirect type radiation detector 28 in which the scintillator 98 converts the radiation X into light, and the converted light generates charges. However, a direct type radiation detector may be provided in which charges are generated by the radiation X.

In the exemplary embodiment described above, explanation has been given regarding a case in which the control section 30 of the console 16 has the functions of a scattered radiation correction data acquisition section, a pixel region acquisition section, an exposure range acquisition section, an image data acquisition section, and a correction section. However, there is no limitation thereto. For example, the imaging control section 22 of the radiographic imaging device 14 may have these functions, or the read control section 50 of the radiographic image reader 18 may have these functions. Moreover, two or more devices out of the imaging control section 22 of the radiographic imaging device 14, the control section 30 of the console 16, and the read control section 50 of the radiographic image reader 18 may include some of the functional sections.

In the present exemplary embodiment, the various programs stored in the imaging control section 22 of the radiographic imaging device 14, the control section 30 of the console 16, the read control section 50 of the radiographic image reader 18, and the irradiation control section 60 of the radiation irradiation device 20 are respectively stored in advance in the ROM of the imaging control section 22, the control section 30, the read control section 50, and the irradiation control section 60. However, there is no limitation thereto. The various programs may be stored in advance on a recording medium such as Compact Disk Read Only Memory (CD-ROM) or a removable disk, and installed on the ROM or the like from the recording medium. Moreover, the various programs may be installed on the ROM or the like from an external device via a communication network such as the internet.

Note that the imaging control section 22, the control section 30, the read control section 50, and the irradiation control section 60 may each be configured by, for example, a semiconductor integrated circuit, and more specifically, by a Field Programmable Gate Array (FPGA), an Application Specific Integrated Circuit (ASIC), or the like.

The radiation X employed in radiographic imaging is not particularly limited, and X-rays, gamma rays or the like may be employed.

Other configurations and operation of the radiographic imaging system 10, the radiographic imaging device 14, the console 16, and the radiographic image reader 18 explained in the present exemplary embodiment are merely examples thereof, and obviously modifications may be made as circumstances dictate within a range not departing from the spirit of the present invention. The image processing described in the present exemplary embodiment is likewise merely an example thereof, and obviously modifications may be made as circumstances dictate within a range not departing from the spirit of the present invention.

What is claimed is:

1. An image processing device comprising:
a scattered radiation correction data acquisition section that acquires scattered radiation correction data as a result of radiation being irradiated onto a radiographic imaging device that images a radiographic image;
a pixel region acquisition section that acquires information indicating a size of an effective pixel region of the radiographic imaging device;
an exposure range acquisition section that acquires information indicating an imaging exposure range of radiation for imaging an imaging subject with the radiographic imaging device;
an image data acquisition section that acquires image data as a result of imaging a radiographic image of the imaging subject; and
a correction section that corrects the image data acquired by the image data acquisition section using the scattered radiation correction data, in a case in which the imaging exposure range includes an area outside of the effective pixel region,
wherein the scattered radiation correction data acquisition section further acquires information indicating a correction exposure range that was irradiated with radiation during acquisition of the scattered radiation correction data, and
wherein the correction section corrects the image data using the scattered radiation correction data based on the size of the correction exposure range and the size of the imaging exposure range.

2. The image processing device of claim 1, wherein the correction section corrects the image data using the scattered radiation correction data, in a case in which the correction exposure range is the same as the imaging exposure range.

3. The image processing device of claim 1, wherein the correction section corrects the image data using the scattered radiation correction data that has been adjusted according to the size of the imaging exposure range, in a case in which the correction exposure range is larger than the imaging exposure range.

4. The image processing device of claim 1, wherein the correction section performs specific processing, in a case in which the correction exposure range is smaller than the imaging exposure range.

5. The image processing device of claim 1, wherein:
there are a plurality of types of the scattered radiation correction, data corresponding to sizes of the correction exposure range; and
the correction section corrects the image data using scattered radiation correction data of a type corresponding to the size of the correction exposure range.

6. The image processing device of claim 1, wherein:
there are a plurality of types of the scattered radiation correction data, corresponding to imaging environment information indicating an imaging environment for imaging the radiographic image; and
the correction section corrects the image data of the radiographic image using scattered radiation correction data of a type corresponding to the imaging environment information indicating an imaging environment in which the radiographic image was imaged.

7. A radiographic imaging system comprising:
a radiation irradiation device including a radiation source and a collimator;
a radiographic imaging device that images a radiographic image using radiation that was irradiated from the radiation irradiation device; and
the image processing device of claim 1, which performs image processing on image data of a radiographic image imaged using the radiographic imaging device.

8. An image processing device comprising:
a scattered radiation correction data acquisition section that acquires scattered radiation correction data as a result of radiation being irradiated onto a radiographic imaging device that images a radiographic image;
a pixel region acquisition section that acquires information indicating a size of an effective pixel region of the radiographic imaging device;
an exposure range acquisition section that acquires information indicating an imaging exposure range of radiation for imaging an imaging subject with the radiographic imaging device;
an image data acquisition section that acquires image data as a result of imaging a radiographic image of the imaging subject; and a correction section that corrects the image data acquired by the image data acquisition section using the scattered radiation correction data, in a case in which the imaging exposure range is larger than the effective pixel region, wherein the scattered radiation correction data acquisition section further acquires information indicating a correction exposure range that was irradiated with radiation during acquisition of the scattered radiation correction data, and wherein the correction section corrects the image data using the scattered radiation correction data based on the size of the correction exposure range and the size of the imaging exposure range.

9. The image processing device of claim 8, wherein the correction section does not correct the image data using the scattered radiation correction data, in a case in which the imaging exposure range is smaller than the effective pixel region.

10. The image processing device of claim 8, wherein the correction section corrects the image data using the scattered radiation correction data, in a case in which the correction exposure range is the same as the imaging exposure range.

11. The image processing device of claim 8, wherein the correction section corrects the image data using the scattered radiation correction data that has been adjusted according to the size of the imaging exposure range, in a case in which the correction exposure range is larger than the imaging exposure range.

12. The image processing device of claim 8, wherein the correction section performs specific processing, in a case in which the correction exposure range is smaller than the imaging exposure range.

13. The image processing device of claim 8, wherein:

there are a plurality of types of the scattered radiation correction data, corresponding to sizes of the correction exposure range; and the correction section corrects the image data using scattered radiation correction data of a type corresponding to the size of the correction exposure range.

14. The image processing device of claim 8, wherein:

there are a plurality of types of the scattered radiation correction data, corresponding to imaging environment information indicating an imaging environment for imaging the radiographic image; and the correction section corrects the image data of the radiographic image using scattered radiation correction data of a type corresponding to the imaging environment information indicating an imaging environment in which the radiographic image was imaged.

15. A radiographic imaging system comprising:

a radiation irradiation device including a radiation source and a collimator;

a radiographic imaging device that images a radiographic image using radiation that was irradiated from the radiation irradiation device; and the image processing device of claim 8, which performs image processing on image data of a radiographic image imaged using the radiographic imaging device.

16. An image processing method comprising:

acquiring, by a scattered radiation correction data acquisition section, scattered radiation correction data as a result of radiation being irradiated onto a radiographic imaging device that images a radiographic image;

acquiring, by a pixel region acquisition section, information indicating a size of an effective pixel region of the radiographic imaging device;

acquiring, by an exposure range acquisition section, information indicating an imaging exposure range of radiation for imaging an imaging subject using the radiographic imaging device;

acquiring, by an image data acquisition section, image data as a result of imaging a radiographic image of the imaging subject; and correcting, by a correction section, the image data acquired by the image data acquisition section using the scattered radiation correction data acquired by the scattered radiation correction data acquisition section, in a case in which the imaging exposure range indicated by the information acquired by the exposure range acquisition section includes an area outside of the effective pixel region indicated by the information acquired by the pixel region acquisition section, and outputting the corrected image data to a memory section or to a display section, wherein the scattered radiation correction data acquisition section further acquires information indicating a correction exposure range that was irradiated with radiation during acquisition of the scattered radiation correction data, and wherein the correction section corrects the image data using the scattered radiation correction data based on the size of the correction exposure range and the size of the imaging exposure range.

17. An image processing method comprising:

acquiring, by a scattered radiation correction data acquisition section, scattered radiation correction data as a result of radiation being irradiated onto a radiographic imaging device that images a radiographic image; acquiring, by a pixel region acquisition section, information indicating a size of an effective pixel region of the radiographic imaging device;

acquiring, by an exposure range acquisition section, information indicating an imaging exposure range of radiation for imaging an imaging subject using the radiographic imaging device; acquiring, by an image data acquisition section, image data as a result of imaging a radiographic image of the imaging subject; and correcting, by a correction section, the image data acquired by the image data acquisition section using the scattered radiation correction data acquired by the scattered radiation correction data acquisition section, in a case in which the imaging exposure range indicated by the information acquired by the exposure range acquisition section is larger than the effective pixel region indicated by the information acquired by the pixel region acquisition section, and outputting the corrected image data to a memory section or to a display section, wherein the scattered radiation correction data acquisition section further acquires information indicating a correction exposure range that was irradiated with radiation during acquisition of the scattered radiation correction data, and wherein the correction section corrects the image data using the scattered radiation correction data based on the size of the correction exposure range and the size of the imaging exposure range.

18. A non-transitory computer readable medium storing an image processing program that causes a computer to execute processing, the processing comprising:

acquiring scattered radiation correction data as a result of radiation being irradiated onto a radiographic imaging device that images a radiographic image;

acquiring information indicating a size of an effective pixel region of the radiographic imaging device;

acquiring information indicating an imaging exposure range of radiation for imaging an imaging subject using the radiographic imaging device;

acquiring image data as a result of imaging a radiographic image of the imaging subject; and correcting the image data using the scattered radiation correction data, in a case in which the imaging exposure range includes an area outside of the effective pixel region, and outputting the corrected image data to a memory section or to a display section, wherein the scattered radiation correction data acquisition section further acquires information indicating a correction exposure range that was irradiated with radiation during acquisition of the scattered radiation correction data, and wherein the correction section corrects the image data using the scattered radiation correction data based on the size of the correction exposure range and the size of the imaging exposure range.

19. A non-transitory computer readable medium storing an image processing program that causes a computer to execute processing, the processing comprising:

acquiring scattered radiation correction data as a result of radiation being irradiated onto a radiographic imaging device that images a radiographic image;

acquiring information indicating a size of an effective pixel region of the radiographic imaging device;

acquiring information indicating an imaging exposure range of radiation for imaging an imaging subject using the radiographic imaging device;

acquiring image data as a result of imaging a radiographic image of the imaging subject; and correcting the image data using the scattered radiation correction data, in a case in which the imaging exposure range is larger than the effective pixel region, and outputting the corrected image data to a memory section or to a display section, wherein the scattered radiation correction data acquisition section further acquires information indicating a correction exposure range that was irradiated with radiation during acquisition of the scattered radiation correction data, and wherein the correction section corrects the image data using the scattered radiation correction data based on the size of the correction exposure range and the size of the imaging exposure range.

\* \* \* \* \*